US011324877B2

(12) United States Patent
Carver

(10) Patent No.: US 11,324,877 B2
(45) Date of Patent: May 10, 2022

(54) AIRWAY ASSIST DEVICE

(71) Applicant: Dechoker LLC, Wheat Ridge, CO (US)

(72) Inventor: Alan R. Carver, Erie, CO (US)

(73) Assignee: Dechoker LLC, Wheat Ridge, CO (US)

( * ) Notice: Subject to any disclaimer, the term of this patent is extended or adjusted under 35 U.S.C. 154(b) by 63 days.

(21) Appl. No.: 16/895,941

(22) Filed: Jun. 8, 2020

(65) Prior Publication Data

US 2020/0306420 A1 Oct. 1, 2020

Related U.S. Application Data

(63) Continuation-in-part of application No. 15/210,944, filed on Jul. 15, 2016, now Pat. No. 10,675,393, which is a continuation-in-part of application No. 14/794,285, filed on Jul. 8, 2015, now abandoned, which is a continuation-in-part of application No. 13/830,574, filed on Mar. 14, 2013, now abandoned, which is a continuation-in-part of application No. 13/135,783, filed on Jul. 15, 2011, now abandoned, which is a continuation-in-part of application No. 12/928,690, filed on Dec. 15, 2010, now abandoned, which is a continuation-in-part of application No. 12/653,645, filed on Dec. 17, 2009, now abandoned.

(51) Int. Cl.
| | |
|---|---|
| *A61M 1/00* | (2006.01) |
| *A61B 17/24* | (2006.01) |
| *A62B 18/02* | (2006.01) |
| *A61M 39/24* | (2006.01) |

(52) U.S. Cl.
CPC ............. *A61M 1/962* (2021.05); *A61B 17/24* (2013.01); *A61M 1/67* (2021.05); *A62B 18/02* (2013.01); *A61M 2039/2406* (2013.01)

(58) Field of Classification Search
CPC ................... A61M 1/67; A61M 1/962; A61M 2039/2406; A62B 18/02; A61B 17/50
See application file for complete search history.

(56) References Cited

U.S. PATENT DOCUMENTS

| | | | | |
|---|---|---|---|---|
| 3,809,079 | A * | 5/1974 | Buttaravoli | ....... A61M 16/0493 128/206.24 |
| 3,939,830 | A | 2/1976 | da Costa | |
| 4,082,095 | A * | 4/1978 | Mendelson | ......... A61M 1/0062 604/38 |
| 4,537,189 | A * | 8/1985 | Vicenzi | ..................... A62B 9/00 128/202.13 |
| 4,971,053 | A * | 11/1990 | Tarrats | ..................... A61M 1/67 128/205.19 |
| 5,313,938 | A | 5/1994 | Garfield et al. | |
| 5,338,166 | A | 8/1994 | Schultz | |
| 5,611,376 | A * | 3/1997 | Chuang | ................. B65B 31/047 141/65 |

(Continued)

OTHER PUBLICATIONS

U.S. Appl. No. 12/653,645, filed Dec. 17, 2009.
U.S. Appl. No. 12/928,690, filed Dec. 15, 2010.
U.S. Appl. No. 13/135,783, filed Jul. 15, 2011.
U.S. Appl. No. 13/830,574, filed Mar. 14, 2013.

(Continued)

*Primary Examiner* — Sarah A Simpson
(74) *Attorney, Agent, or Firm* — Craig R. Miles; CR Miles P.C.

(57) ABSTRACT

An airway assist device and methods of making and using an airway assist device to assist in opening an airway or removing fluid or material obstructing an airway of a subject.

15 Claims, 12 Drawing Sheets

(56) References Cited

U.S. PATENT DOCUMENTS

| | | | |
|---|---|---|---|
| 7,387,062 B2* | 6/2008 | Chen | F15B 15/1447 92/172 |
| 2005/0085799 A1* | 4/2005 | Luria | A61M 16/0009 606/1 |
| 2007/0251528 A1* | 11/2007 | Seitz | A62B 18/02 128/205.25 |
| 2009/0175747 A1 | 7/2009 | LeBoeuf et al. | |
| 2009/0228018 A1 | 9/2009 | Winiarski | |
| 2011/0152794 A1* | 6/2011 | Carver | A61M 1/0011 604/275 |
| 2012/0221010 A1 | 8/2012 | DeLuca et al. | |
| 2015/0190158 A1 | 7/2015 | Lih | |
| 2019/0150962 A1* | 5/2019 | Cutino | A61B 1/06 |
| 2020/0306420 A1 | 10/2020 | Carver | |

OTHER PUBLICATIONS

U.S. Appl. No. 14/794,285, filed Jul. 8, 2015.
U.S. Appl. No. 15/210,944, filed Jul. 15, 2016.
U.S. Appl. No. 15/210,944; Office Action dated Feb. 10, 2017.
U.S. Appl. No. 15/210,944; Office Action dated Sep. 20, 2017.
U.S. Appl. No. 15/210,944; Office Action dated Jan. 12, 2018.
U.S. Appl. No. 15/210,944; Office Action dated Jun. 22, 2018.
U.S. Appl. No. 15/210,944; Office Action dated May 20, 2019.
U.S. Appl. No. 15/210,944; Appeal Brief filed Feb. 21, 2019.
PCT International Patent Application No. PCT/US21/36216, International Search Report and Written Opinion of the International Searching Authority dated Oct. 1, 2021, 14 pages.
Amazon. Dechoker Anti-Choking Device for Adults (Ages 12 Years and up). Website, https://www.amazon.com, review from Oct. 21, 2019, originally downloaded Aug. 10, 2021, 11 pages.

* cited by examiner

AIRWAY ASSIST DEVICE

This United States patent application is a continuation-in-part of U.S. patent application Ser. No. 15/210,944, filed Jul. 15, 2016, now U.S. Pat. No. 10,675,393, issued Jun. 9, 2020, which is a continuation-in-part of U.S. patent application Ser. No. 14/794,285, filed Jul. 8, 2015, which is a continuation-in-part of U.S. patent application Ser. No. 13/830,574, filed Mar. 14, 2013, which is a continuation-in-part of U.S. patent application Ser. No. 13/135,783, filed Jul. 15, 2011, which is a continuation-in-part of U.S. patent application Ser. No. 12/928,690, filed Dec. 15, 2010, which is a continuation-in-part of U.S. patent application Ser. No. 12/653,645, filed Dec. 17, 2009, each hereby incorporated by reference herein.

I. FIELD OF THE INVENTION

An airway assist device and methods of making and using an airway assist device to assist in opening an airway or removing fluid or material obstructing an airway of a subject.

II. BACKGROUND OF THE INVENTION

A chocking person alone may not be able to perform the Heimlich maneuver on himself or herself. Another person if present may lack the physical strength, be untrained, or be too afraid to perform the Heimlich maneuver on the chocking person.

There would be a substantial advantage for a chocking person to have access to an airway assist device that can be readily used with or without assistance of another person to open the airway when chocking.

III. SUMMARY OF THE INVENTION

A broad object of particular embodiments of the invention can be to provide an airway assist device including a barrel having an open barrel proximal end and a barrel distal end having a first opening and a second opening. A plunger having a plunger proximal end and a plunger distal end slidably moves within said barrel. A first one-way valve fluidically coupled to the first opening at the barrel distal end allows fluid or materials to pass into the barrel upon outward draw of the plunger in the barrel and a second one-way valve fluidically coupled to the second opening allows fluid or materials to pass out of the barrel upon inward push of the plunger in said barrel. A throat tube fluidically coupled to the first opening passes through a face mask configured to engage the face of a subject with the throat tube inserted into the airway of the subject. A receptacle fluidically coupled to the second opening receives fluid or materials drawn or dislodged from the subject's airway.

Another broad object of particular embodiments of the invention can be to provide an airway assist device including a barrel having an open barrel proximal end and a barrel distal end having an opening. A plunger having a plunger proximal end and a plunger distal end slidably moves within said barrel. A first concentric ring, a second concentric ring and a third concentric ring disposed in spaced apart relation encircle the plunger proximate said plunger distal end. A first seal encircles the plunger between said first concentric ring and said second concentric ring and a second seal encircles the plunger between the second concentric ring and the third concentric ring. A one-way valve fluidically coupled to the first opening at the barrel distal end allows fluid or materials to pass into the barrel upon outward draw of the plunger in the barrel. A throat tube fluidically coupled to the opening passes through a face mask configured to engage the face of a subject with the throat tube inserted into the airway of the subject.

Another broad object of embodiments of the invention can be a method of making an airway assist device including forming a barrel having an open barrel proximate end opposite a barrel distal end having a first opening and a second opening and slidably engaging a plunger within said barrel. Fluidically coupling a first one-way valve to said first opening at said barrel distal end through which fluid passes into said barrel upon outward draw of said plunger in said barrel and fluidically coupling a second one-way valve to the second opening through which fluid passes out of said barrel upon inward push of said plunger in said barrel. Fluidically coupling a throat tube to the first opening which passes through a face mask configured to engage the face of a subject with the throat tube inserted into the airway of the subject. Fluidically coupling a receptacle to the second opening to receive fluid or materials drawn or dislodged from the subject's airway.

Another broad object of particular embodiments of the invention can be a method of using an airway assist device including slidably engaging a plunger in a barrel, wherein the barrel has a barrel distal end including a first opening including a first one-way valve which allows fluid and materials to pass into the barrel upon outwardly drawing the plunger in the barrel, and a second one-way valve which allows fluid to pass from the barrel upon inwardly pushing of the plunger in the barrel. Fluidically coupling a throat tube which passes through a face mask to the first opening. Inserting throat tube into an airway of a subject and engaging the mask about the mouth and nose of the subject and outwardly drawing the plunger slidably disposed within said barrel to generate a suction in throat tube, and drawing fluid or material under said suction from said throat of the subject into the barrel.

Naturally, further objects of the invention are disclosed throughout other areas of the specification, drawings, photographs, and claims.

IV. BRIEF DESCRIPTION OF THE DRAWINGS

V. DETAILED DESCRIPTION OF THE INVENTION

Figure 1:
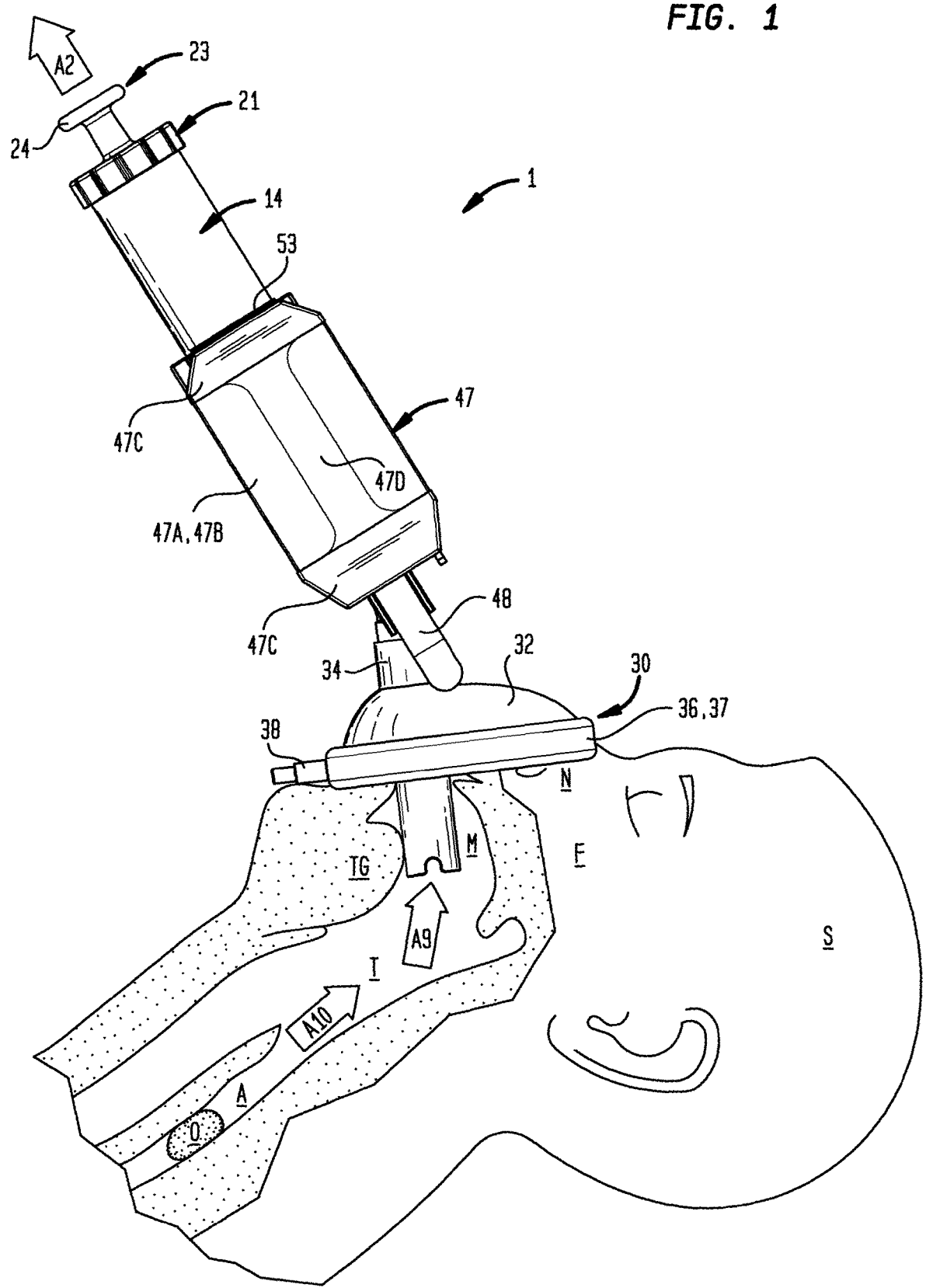
FIG. 1 is an illustration of a method of using a particular embodiment of the airway assist device.

Now, with general reference to FIGS. 1 through 12 which depict embodiments of an airway assist device (1) and methods of making embodiments of an airway assist device (1) and using embodiments of the airway assist device (1) to assist in opening an airway (A) or removing fluid or material (O) obstructing the airway (A) of a subject (S).

Now, with primary reference to FIGS. 2 through 12, embodiments of the airway assist device (1) can comprise, consist essentially of or consist of one or more of the components further described herein. Embodiments can include a barrel (2) having an open barrel proximal end (3) and a barrel distal end (4). In particular embodiments, the barrel distal end (4) can include a first opening (5) and can further include a second opening (6) communicating between a barrel external surface (7) and a barrel internal surface (8) which defines a barrel interior chamber (9). In particular embodiments, a retainer ring (10) having a radially inwardly directed annular lip (11) which defines a retainer ring opening (12) can, but need not necessarily, be removably coupled to the barrel proximal end (3). While the Figures depict rotatably mateable threads (13) disposed on the barrel proximal end (3) and the retainer ring (11), this is not intended to preclude embodiments which otherwise removably secure the retainer ring (11) to the barrel proximate end (3), for example: friction fit, snap fit, detent, clasps, bullet catch, or the like, or combinations thereof.

Again, with primary reference to FIGS. 2 through 12, embodiments can further include a plunger (14) slidably disposed within the barrel interior chamber (9) of the barrel (2). The plunger (14) can have a length disposed between a plunger proximal end (15) and a plunger distal end (16). In particular embodiments, the plunger (14) can comprise a plunger sidewall (17) having a plunger external surface (18) and a plunger internal surface (19) joining a closed plunger distal end (16) defining a plunger interior chamber (20) open at the plunger proximal end (15). In particular embodiments, the plunger (14) can further include a plunger cap (21) coupled or removably coupled to the plunger proximal end (15).

While the Figures depict rotatably mateable threads (22) disposed on the plunger proximal end (15) and the plunger cap (21), this is not intended to preclude embodiments which otherwise removably secure the plunger cap (21) to the plunger proximate end (15), for example: friction fit, snap fit, detent, clasps, bullet catch, or the like, or combinations thereof.

Figure 4:
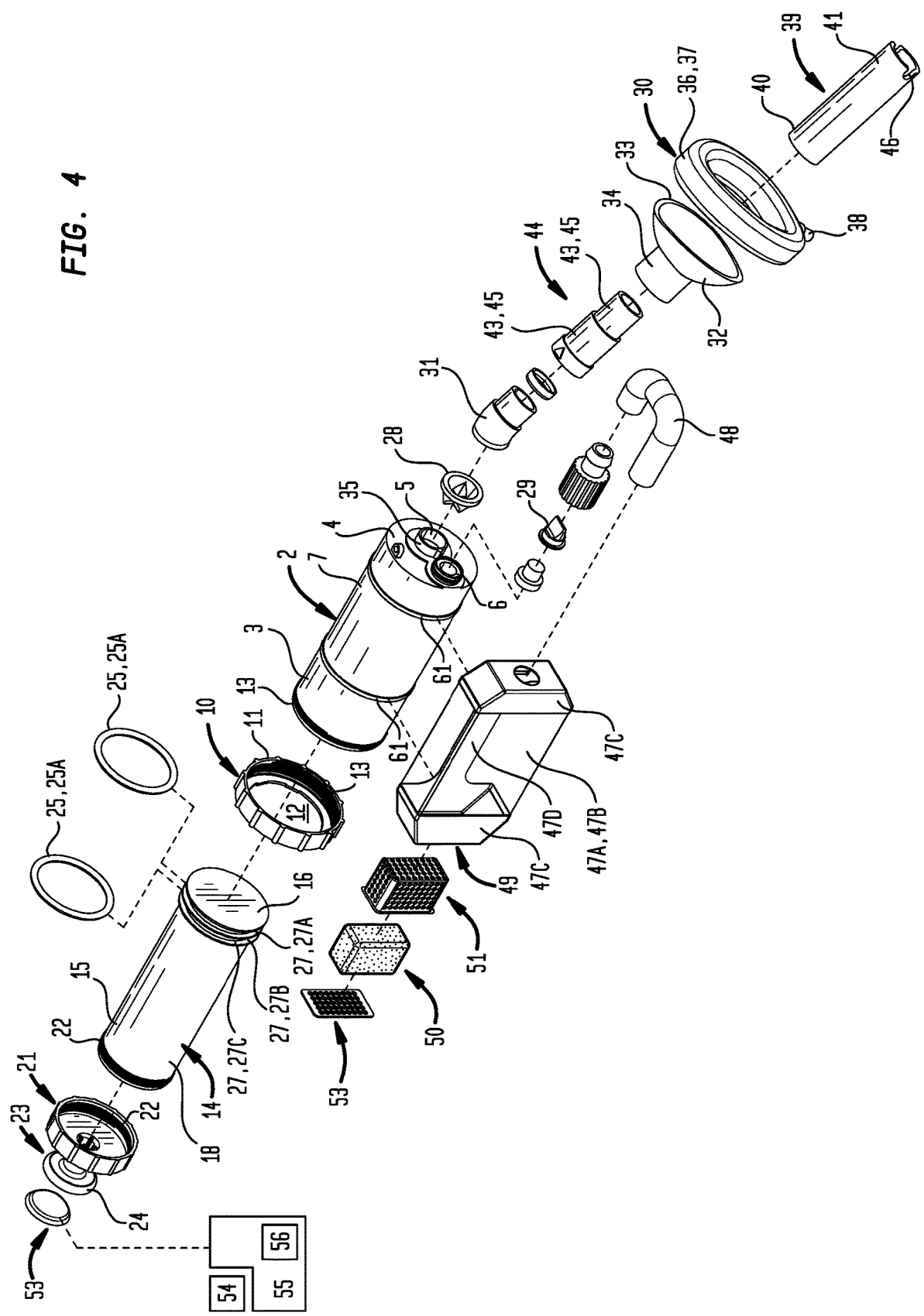
FIG. 4 is an exploded view of a particular embodiment of the airway assist device.
Figure 5:
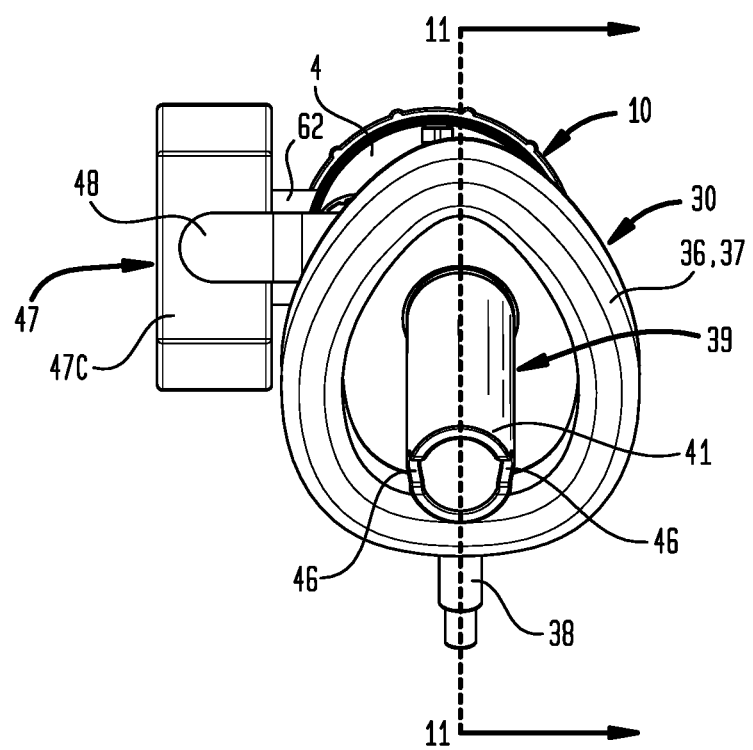
FIG. 5 is first end elevation view of a particular embodiment of the airway assist device.
Figure 6:
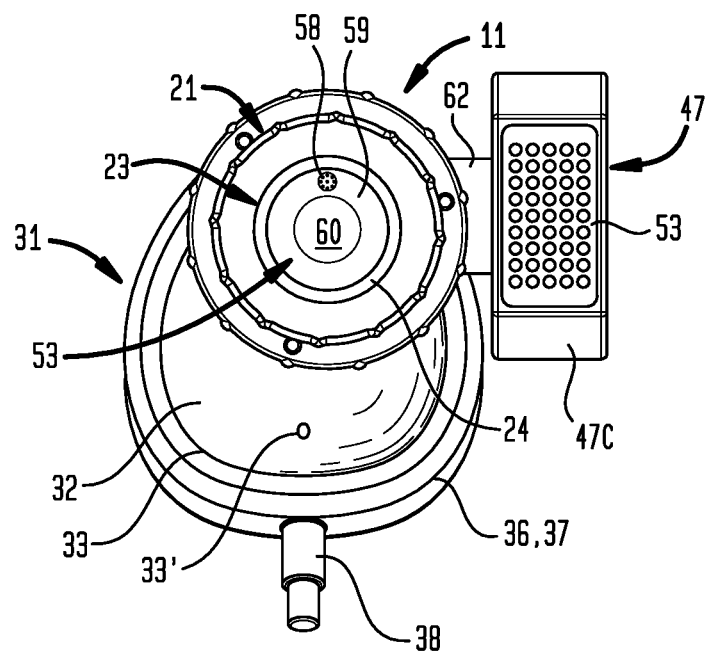
FIG. 6 is a second end elevation view of a particular embodiment of the airway assist device.
Figure 7:
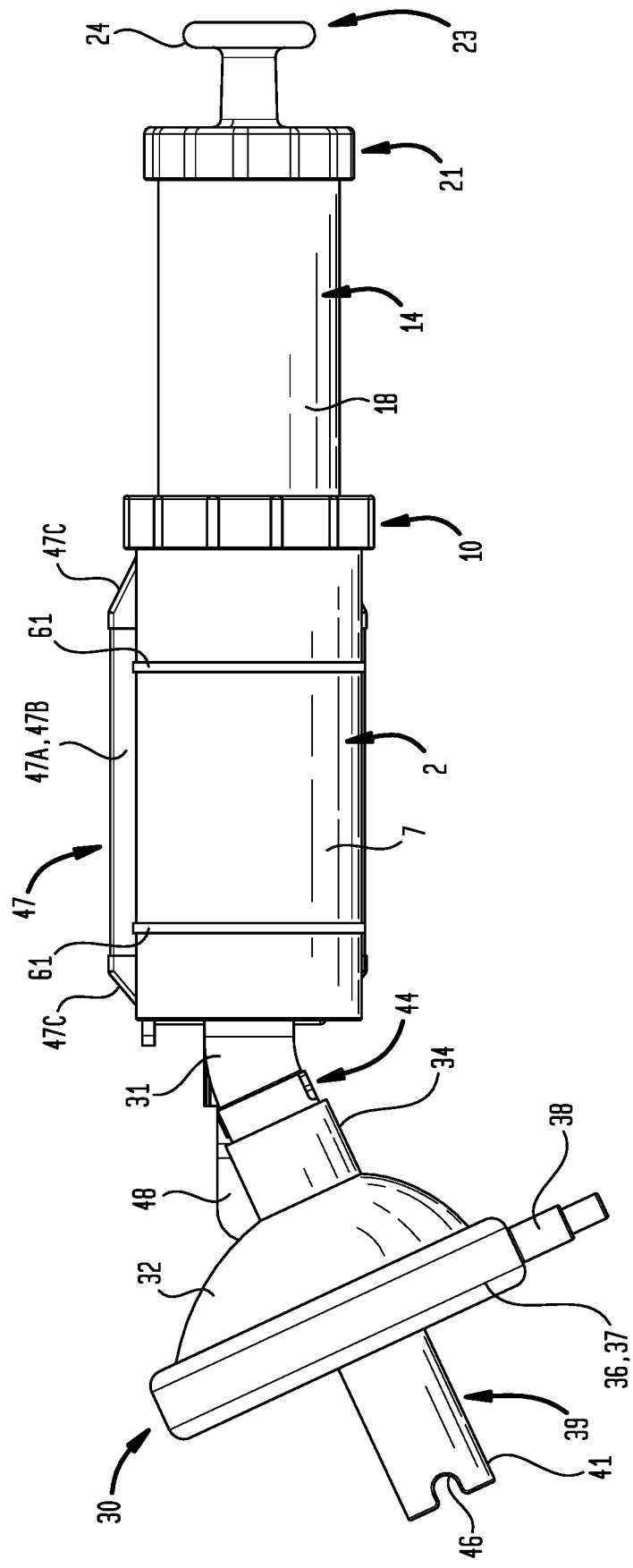
FIG. 7 is first side elevation view of a particular embodiment of the airway assist device.
Figure 8:
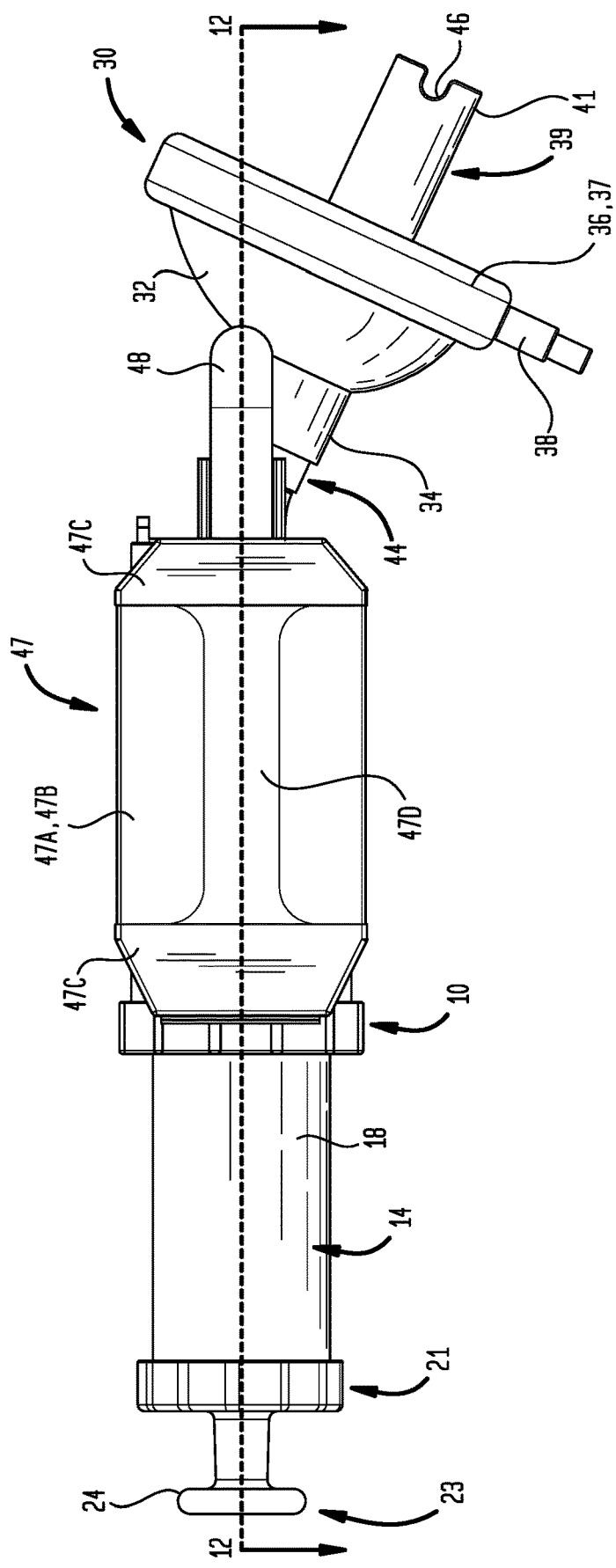
FIG. 8 is a second side elevation view of a particular embodiment of the airway assist device.

Now, with primary reference to FIG. 4, in particular embodiments, upon inward movement of the plunger (14) in the barrel (2), the surfaces of the barrel distal end (4) and the plunger distal end (16) can, but need not necessarily, be configured to engage or abut. As one illustrative example, the plunger distal end (16) can be substantially flat or flat and the barrel internal surface (8) at the barrel distal end (4) can be substantially flat or flat allowing the barrel distal end (14) to abut the barrel internal surface (8) at barrel distal end (4). Additionally, while the barrel (2) and the plunger (14) can have linear parallel sides and a circular cross section, this is not intended to preclude embodiments of the barrel (2) and the plunger (14) having non-linear sides or a non-circular cross section, such as: an oval, a square, a rectangular or other polygonal or non-polygonal cross section.

Now, with primary reference to FIGS. 2 through 12, embodiments can, but need not necessarily, include a handle (23) coupled to the plunger proximal end (15) of the plunger (14). In particular embodiments, the handle (23) can be configured as a knob (24) as depicted in the Figures, but this is not intended to preclude any configuration which can be grasped to aid in sliding the plunger (14) within the barrel (2). In particular embodiments, the handle (23) can be coupled to the plunger cap (21). The handle (23) and the plunger cap (21) can, but need not necessarily be, one-piece.

In particular embodiments, one or more seals (25) can, but need not necessarily, encircle the plunger (14) proximate the plunger distal end (16) and contact the barrel internal surface (8) upon sliding engagement of the plunger (14) in the barrel (2). In the particular embodiments shown by the Figures, a first seal (25A) and a second seal (25B) can be disposed in spaced apart relation each encircling the plunger (14) proximate the plunger distal end (16). The seals (25) can be configured as any form of mechanical gasket which can be affixed or removably affixed to the plunger (14) and compressed between the barrel (2) and barrel internal surface (8) to reduce transfer of air in the annular space (26) between the plunger (14) and the barrel internal surface (8). In particular embodiments, the one or more seals (25) can comprise one or more O-rings.

In particular embodiments, the plunger (14) can, but need not necessarily, further include one or more concentric rings (27) radially extending from and encircling the plunger (14) proximate the plunger distal end (16). The term "concentric rings" broadly encompasses a continuous concentric ring (27) or concentric ring segments which partially encircle the plunger (14). In particular embodiments, a first concentric ring (27A) can be disposed to encircle and radially extend the plunger distal end (16) of the plunger (14). As shown in the illustrative example of FIG. 4 the first concentric ring (27A) can extend the flat or substantially flat surface of the plunger distal end (16). In other particular embodiments, a first concentric ring (27A) and a second concentric ring (27B) can be disposed in spaced apart relation proximate the plunger distal end (16) with the first seal (25A) encircling the plunger (14) disposed between the first concentric ring (27A) and the second concentric ring (27B). In other particular embodiments, a first concentric ring (27A) and a second concentric ring (27B) and a third concentric ring (27C) can be disposed in spaced apart relation proximate the plunger distal end (16) of the plunger (14) with the first seal (27A) encircling the plunger (14) disposed between the first concentric ring (27A) and the second concentric ring (27B) and the second seal (25B) encircling the plunger (14) disposed between the second concentric ring (27B) and the third concentric ring (27C). As shown in the illustrative example of FIG. 4, one or more of the concentric rings (27) can, but need not necessarily, extend sufficiently radially outward of the plunger (14) to engage the inwardly directed lip (11) of the retainer ring (10) upon outward draw of the plunger (14) in the barrel (2) prevent the plunger (14) from being removed from the barrel (2).

Figure 11:
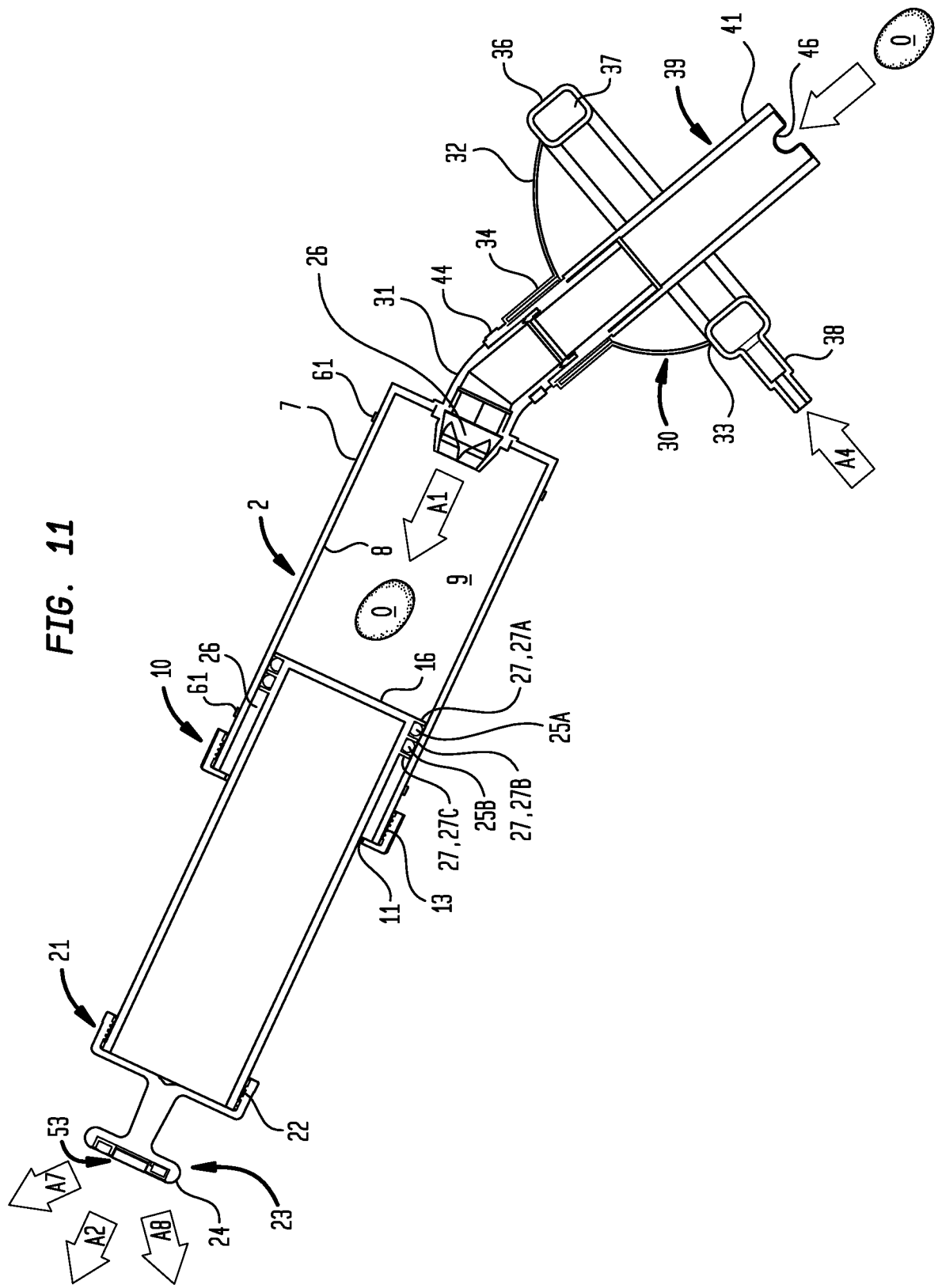
FIG. 11 is cross section view 11-11 as shown in FIG. 5 which illustrates a particular method of use of the airway assist device.
Figure 12:
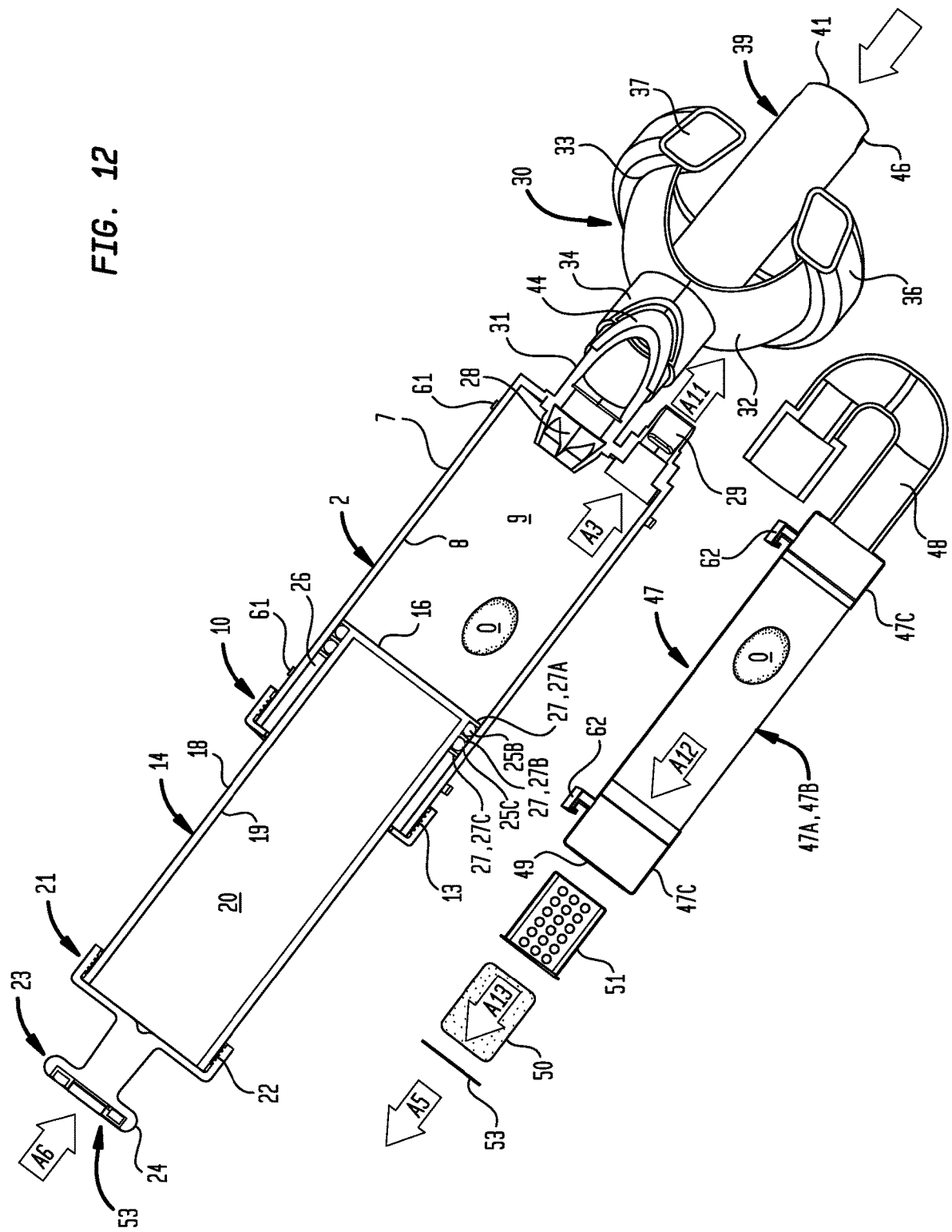
FIG. 12 is a cross section view 12-12 as shown in FIG. 8 which illustrates a particular method of use of the airway assist device.

Now, with primary reference to FIGS. 4 and 11 through 12, in particular embodiments, a first one-way valve (28) can, but need not necessarily, be disposed to regulate airflow (depicted as arrow A1) through the first opening (5) in the barrel distal end (4). The first one-way valve (28) can reduce or prevent airflow from passing outward of the first opening (5) from the barrel interior chamber (9) when the plunger (14) moves inward (depicted as arrow A2) within the barrel (2) toward the barrel distal end (4)(as shown in the example of FIG. 11). In other particular embodiments, a second one-way valve (29) can, but need not necessarily, be disposed to regulate airflow (depicted by arrow A3) through the second opening (29) in the barrel distal end (4) of the barrel (2)(as shown in the example of FIG. 12). The second one-way valve (29) can reduce or prevent airflow from passing inward of the second opening (6) into the barrel interior chamber (9) when the plunger (14) moves outward (depicted by arrow A2) within the barrel (2) toward the barrel proximal end (3). In particular embodiments, the first one-way valve (28) or the second one-way valve (29) can, but need not necessarily be, duck bill valves as depicted in the Figures and the first and second valves (28)(29) can be in the form of any type of one way valve, such as: check valves, clack valves, non-return valves, reflux valves, retention valves, diaphragm valves, ball check valves, swing check valve, flapper valves or the like.

Now, with primary reference to FIGS. 4 and 11 through 12, in particular embodiments, with the retainer ring (10) removed from the barrel proximal end (3) of the barrel (2), the plunger distal end (16) can be inserted into the barrel interior chamber (9) of the barrel (2). With the plunger (14) inserted into the barrel (2), the retainer ring (10) can be passed over plunger proximal end (15) and mateably secured or threadably coupled to the barrel proximal end (3) of the barrel (2). The plunger (14) can slide within the barrel interior chamber (9) of the barrel (2). In particular embodiments, the plunger (14) can be pushed inward within the barrel interior chamber (9) to abut the plunger distal end (16) with the barrel internal surface (7) at the barrel distal end (4) of the barrel (2). In this position, the barrel proximal end (3) of the plunger (2) or the handle (23) can extend through the retainer ring opening (12) out of the barrel proximal end (3) of the barrel (2). During outward draw of the plunger (14) within the barrel (2), the plunger, the plunger and one or more seals (25), or the plunger and one or more seals disposed between the corresponding concentric rings (27), can inhibit air flowing in the annular space (26) between the plunger (14) and the barrel internal surface (8) of the barrel (2). The plunger (14) can act as a piston to reduce pressure within the barrel interior chamber (9) of the barrel (2). The reduced pressure causes air to enter the barrel interior chamber (9) (depicted by arrow A1) through the first opening (5) disposed in the barrel distal end (4) or through the first one-way valve (28). In those embodiments, having a first and second one-way valves (28)(29), the second one-way valve (29) precludes or reduces airflow from passing through the second opening (6) into the barrel interior chamber (9). Conversely, during movement of the plunger (14) toward the barrel distal end (4) the plunger (14) acts as a piston to increase pressure within the barrel interior chamber (9) of the barrel (2). The increased pressure causes air to egress from the barrel interior chamber through the second opening (6) in the barrel distal end (4) or through the second one-way valve (29). In those embodiments, having a first and second one-way valves (28)(29), the first one-way valve (28) precludes or reduces airflow from passing through the first opening (5) from the barrel interior chamber (9).

Now, with primary reference to FIGS. 1 through 12, in particular embodiments, a face mask (30) can be fluidically coupled to the first opening (5) in the barrel distal end (4) directly or through one or more hollow connectors (31). In the illustrative example of FIGS. 1 and 4, the face mask (30) can include a dome (32) extending to a dome outer periphery (33) which can be configured to engage a subject (S). A hollow stem (34) can outwardly extend from the dome (32) of the face mask (30) and be configured to removably couple directly or indirectly through one or more hollow connectors (31), with a tubular extension (35) disposed about the first opening (5) in the barrel distal end (4) of the barrel (2). A small aperture (38) can be disposed in the face mask (30) to assist in preventing over pressurization of the face mask (30). In particular embodiments, the face mask (30) can, but need not necessarily, include a plurality of face masks (30) which can be of the same size, or can have a range of different sizes to correspondingly engage a plurality of subjects (S) of different sizes. Accordingly, a plurality of face masks (30) can be interchangeably coupled to the barrel (3) for the purposes of replacement of lost or damaged face masks, maintain sterile conditions, or to fit the features or size of each of a plurality of subjects (S). In particular embodiments, the dome outer periphery (33) can, but need not necessarily, engage an annular cuff (36). The annular cuff (36) can comprise a solid material having a density, hardness, or compression, or combination thereof, to conform to the subject's face (F) about the mouth (M) and nose (N) as shown in the illustrative example of FIG. 1.

Now with primary reference to FIGS. 1 and 11 and 12, in particular embodiments, the annular cuff (36) can comprise an inflatable tubular member (37). The tubular member (37) can be inflated (depicted by arrow A4) to a firmness that allows the annular cuff (36) to conform to the subject's face (F) about the mouth (M) and nose (N). An inflatable annular cuff (36) can confer substantial advantages by engaging the subject's face (F) with a better fit or seal to retain the reduced pressure or suction generated during operation of the plunger (14) within the barrel (2), or to afford greater comfort to the subject (S). In particular embodiments, the annular cuff (36) can include a sealable fluid port (38) through which a fluid can ingress and egress the annular cuff (36) (depicted by arrow A4) to allow the firmness of the annular cuff (36) to be adjusted or to allow shipment in a deflated condition. In particular embodiments, the dome (32) can comprise a sufficiently transparent or clear material allowing observation of the subject (S) or the fluid or material (O) drawn up from a throat (T) of the subject (S) through the dome (32).

Now, with primary reference to FIG. 4, a throat tube (39) having a length disposed between a throat tube first end (40) and a throat tube second end (41) can be coupled to or pass through the hollow stem (34) of the face mask (30) to directly, or indirectly through one or more hollow connectors (31), be fluidically coupled to the first opening (5) in the barrel distal end (4) of the barrel (2). In the illustrative example of FIG. 4, the hollow stem (34) extending outward of the dome (32) of the face mask (30) slidably engages a first portion (42) of a first hollow connector external surface (43) of a first hollow connector (44). A second portion (45) of the first hollow connector external surface (43) having a lesser dimension passes through the hollow stem (34) and slidably receives the throat tube first end (40). The assembly of the first hollow connector (44), the face mask (30), and the throat tube (39) can be fluidically connected to the first opening (5) in the barrel distal end (4) to fluidically couple the throat tube second end (41) to the barrel interior chamber (9). In particular embodiments, the throat tube (39) can pass through the hollow stem (34) of the face mask (30) and directly, or indirectly through one or more hollow connectors (31) fluidically couple to the first opening (5) at the barrel distal end (4) of the barrel (2). In particular embodiments, the hollow stem (34) and the throat tube (39) can be one piece.

Figure 2:
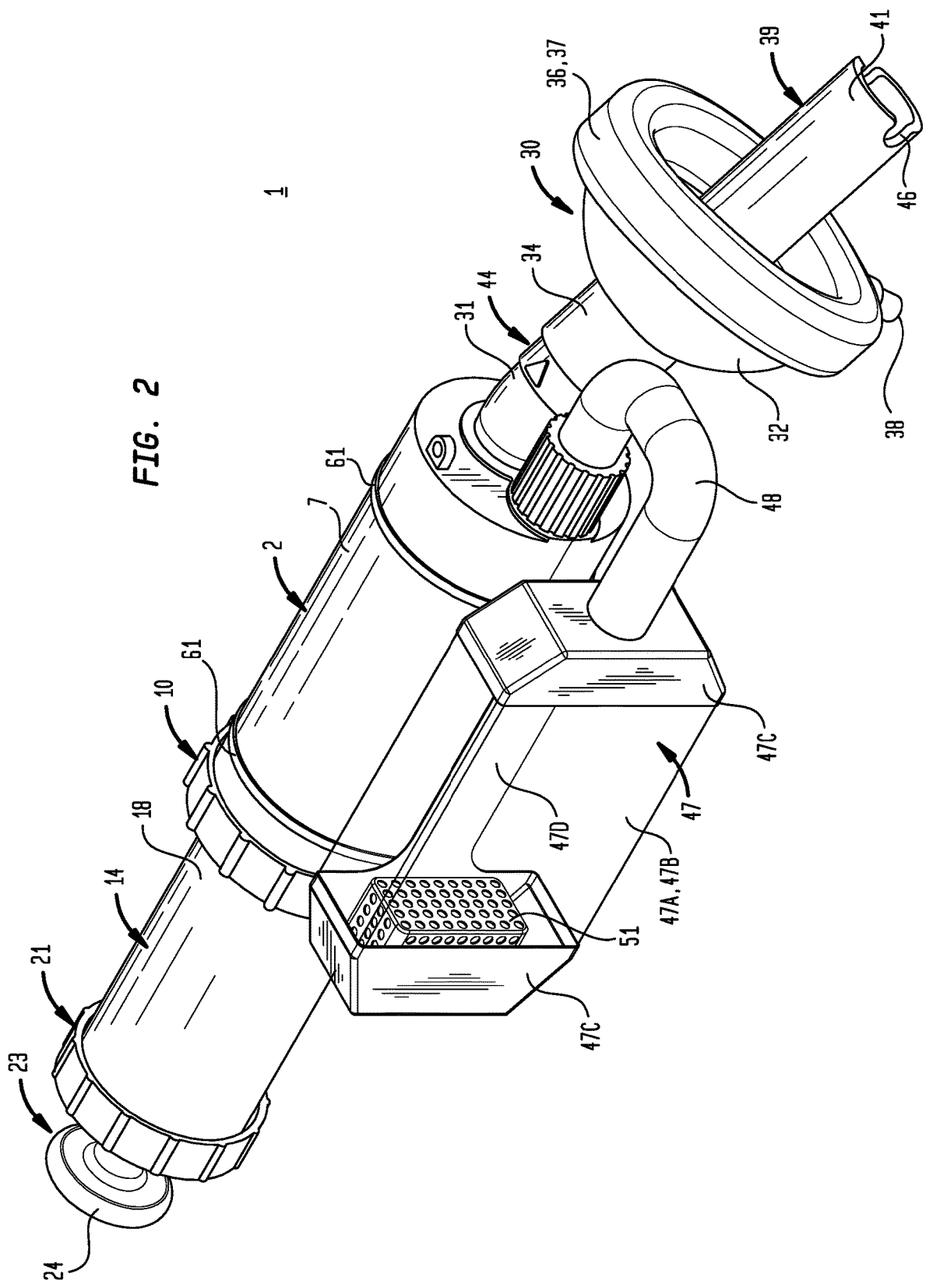
FIG. 2 is a first perspective view of a particular embodiment of the airway assist device.
Figure 3:
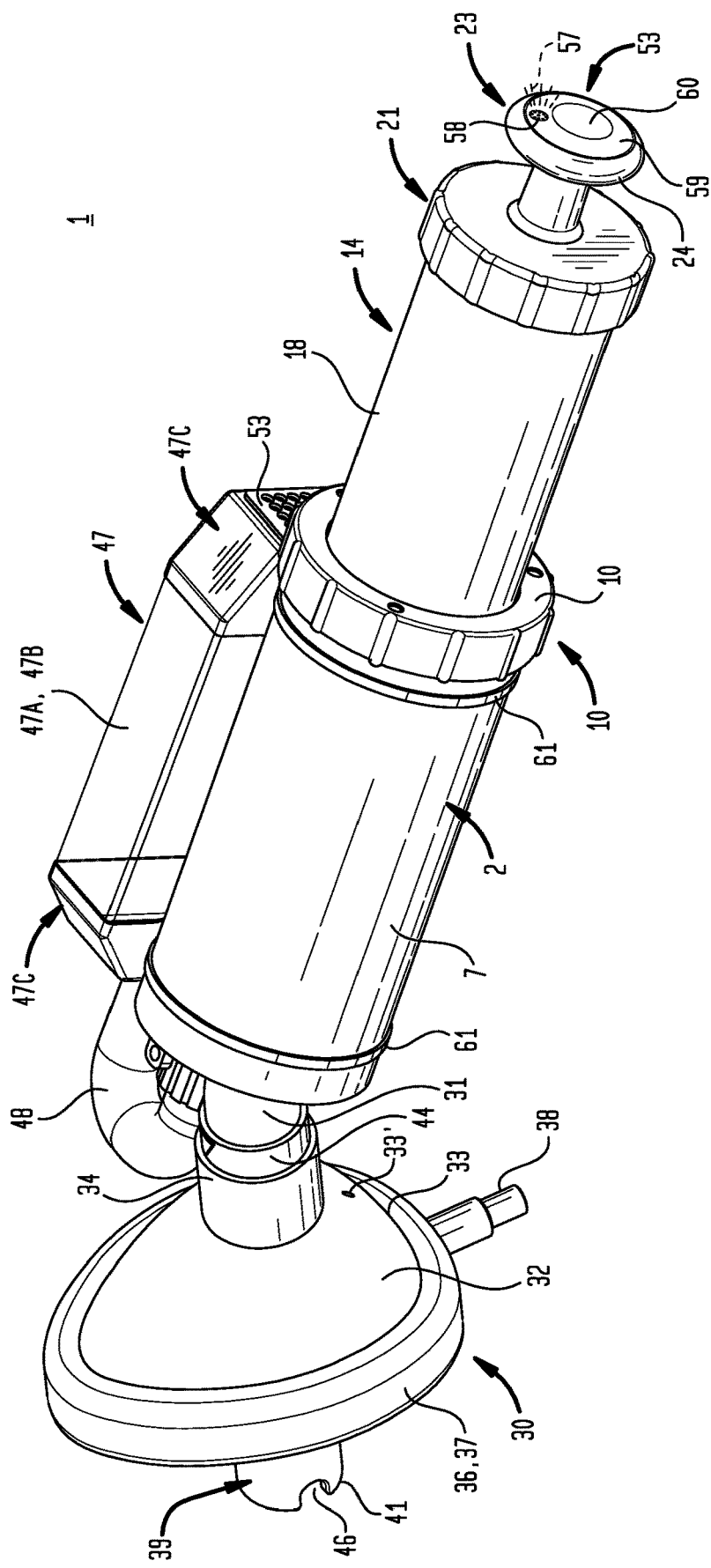
FIG. 3 is second perspective view of a particular embodiment of the airway assist device.

Now, with primary reference to FIGS. 1 and 2, in particular embodiments, the throat tube (39) can, but need not necessarily, include or more notches (46) open to the throat tube second end (41). The one or more notches (46) can assist in preventing the tongue (T) of the subject (S) from being drawn by suction into the throat tube second end (41) during outward movement of the plunger (14) in the barrel (2). In particular embodiments, the throat tube (39) can curve approaching the tube second end (41) to assist in advancement of the throat tube (39) into the curvature of the airway (A). The throat tube (39) can, but need not necessarily, comprise a resilient or pliant material, as examples: polyvinylchloride, polyethylene, polypropylene, polyurethane, rubber, silicone, or neoprene and combinations thereof.

Now, with primary reference to FIGS. 2 through 10, embodiments can, but need not necessarily include, a receptacle (47) fluidically coupled directly, or indirectly through one or more hollow connectors (48), to the second opening (6) in the barrel distal end (4) of the barrel (2). The fluid or materials (O) contained within the barrel interior chamber (9) can, by inward movement of the plunger (14) in the barrel (2), be transferred through the second opening (5) in the barrel distal end (4) and collected in the receptacle (47). In particular embodiments, the receptacle (47) can comprise a flexible receptacle (47A) which may be disposed of after use, while in other embodiments, the receptacle can be a rigid receptacle (47B) which can be periodically cleaned and recoupled to the second opening (5) in the barrel distal end (4) of the barrel (2). In the illustrative example of the Figures, the receptacle (47) includes a flexible receptacle (47A) disposed between a pair of rigid receptacle end caps (47C) disposed a fixed distance apart by a cross member (47D). The flexible receptacle (47A) can comprise a sufficiently transparent material to visually observe the fluid and materials (O) contained in the receptacle (47).

Now with primary reference to FIGS. 2 and 12, in particular embodiments, the receptacle (47) can further include a fluid outlet port (49) to allow egress of air from the receptacle (47) (depicted by arrow A5) upon inward movement of plunger (14) in the barrel (2)(depicted by arrow A6). In particular embodiments, the fluid outlet port (48) can comprise an aperture (49) in the receptacle (47). In other embodiments, the fluid outlet port (48) can be configured to receive or couple to a filter (50). The filter (50) can comprise one or more filter layers affixed to or over the fluid outlet port (48). The filter can, but need not necessarily, selectively allow air to pass out of the receptacle (47) but, retain liquids and materials (O) inside of the receptacle (47). As one illustrative example, the filter (50) can comprise a fine mesh of woven polyester plastic monofilament treated with a hydrophobic coating which allows air and sound to pass but precludes, liquids and materials (O) from passing through the mesh which can be obtained from Futation, Hammerensgade 1, 2.th, 1267 Copenhagen, Denmark. Similarly, the filter (50) can comprise a porous membrane comprising a fluoroplastic such as tetrafluoroethylene which can be obtained through ThermoFisher Scientific 168 Third Avenue, Waltham, Mass. 02451. Additionally, the filter (50) can optionally comprise a porous foam material; however, these illustrative examples are not intended to preclude filters (50) made from other suitable materials, such as: cellulose acetate, polyethersulfone, nylon, cellulose nitrate, glass fiber or the like and combinations thereof.

Again, with primary reference to FIGS. 2 and 12, a perforated filter retainer (51) can be coupled to the fluid outlet port (48) to provide a filter retainer interior chamber (52). A filter (50) can be retained or removably retained within the filter retainer interior chamber (52) of the perforated filter retainer (51). A perforated filter retainer closure (53) can be removably coupled or immovably affixed to the perforated filter retainer (51) to retain the filter (5) within the filter retainer interior chamber (52). The perforated filter retainer (51) and the perforated filter retainer closure (53) can be configured to contact the filter (50) to reduce or prevent liquids or materials (O) from passing around the filter (50).

Figure 9:
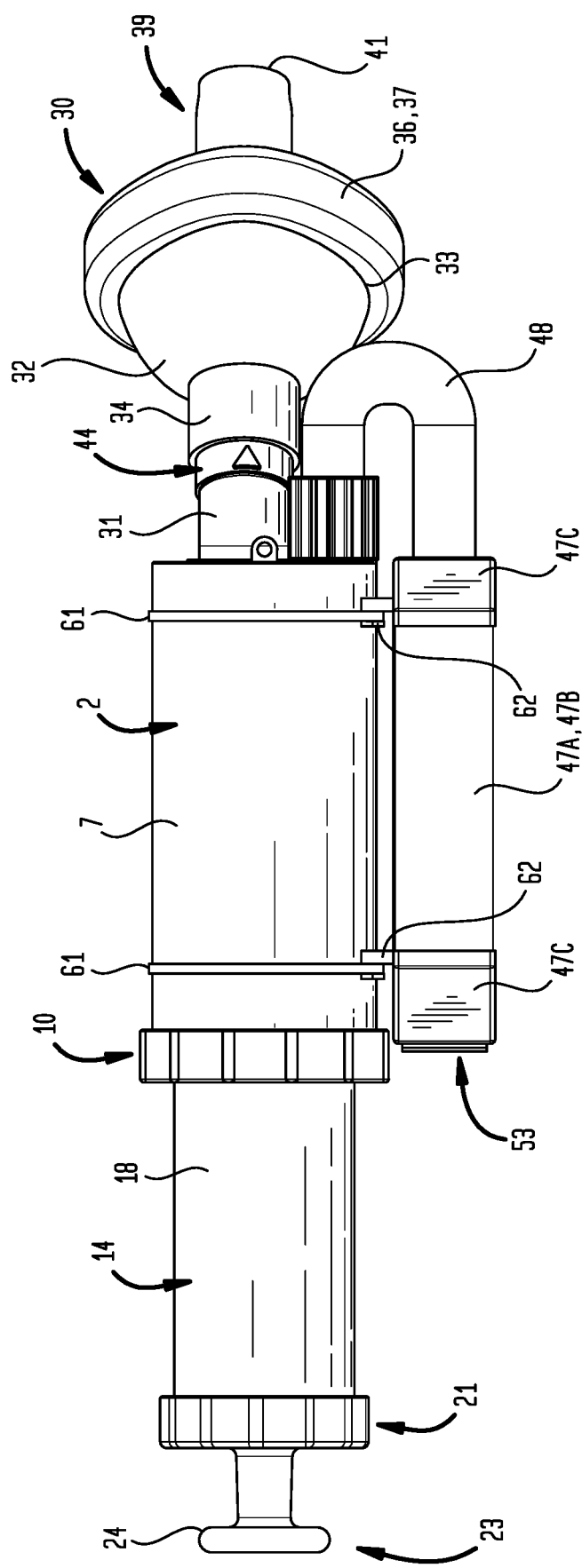
FIG. 9 is top plan view of a particular embodiment of the airway assist device.
Figure 10:
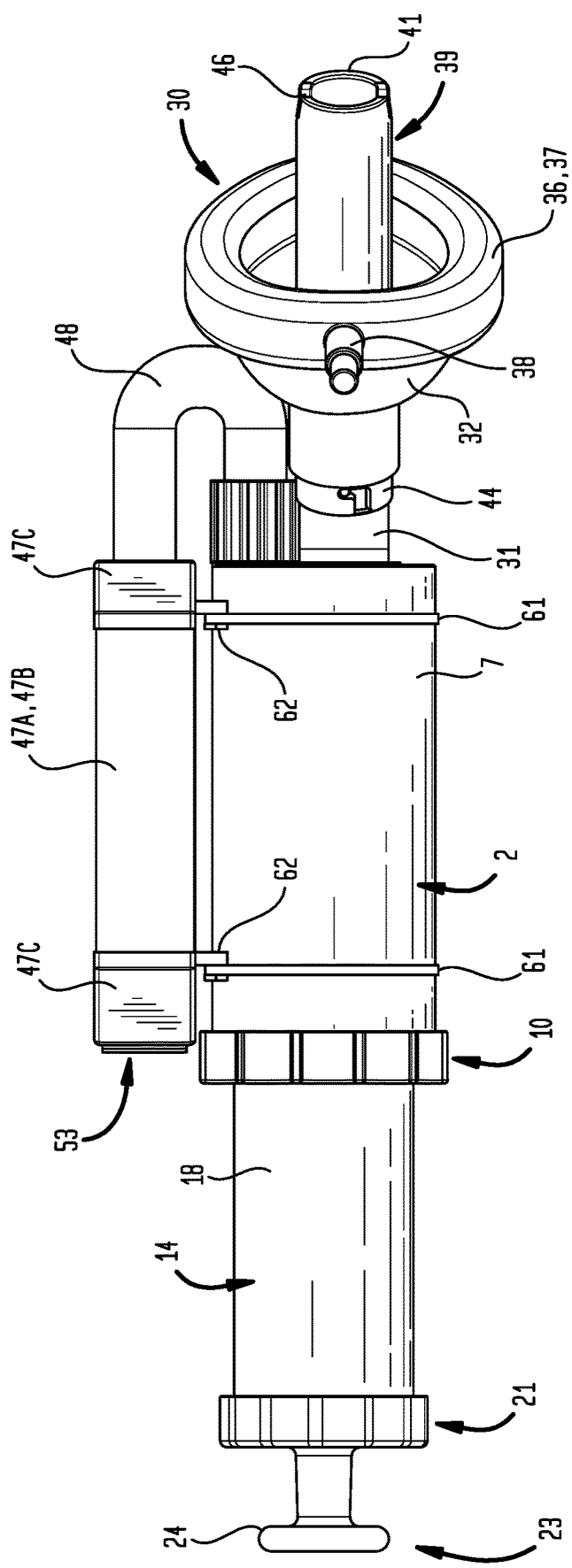
FIG. 10 is bottom plan view of a particular embodiment of the airway assist device.

Now with primary reference to FIG. 9, in particular embodiments, the receptacle (47) can, but need not necessarily, be coupled to the barrel (2) of the airway assist device (1). As an illustrative example, one more receptacle retention bands (61) can circumferentially engage the barrel (2) and be sufficiently elastic to couple or removably couple to one or more receptacle retainers (62) to couple or removably couple the receptacle (47) to the barrel (2) of the airway assist device (1); however, this illustrative example is not intended to preclude the use of other embodiments to couple or removably couple the receptacle (47) to the airway assist device (1), including as example mated pairs of fittings which friction fit, snap fit, interleave, threadably engage, or the like.

Now, with primary reference to FIGS. 3, 4, 11, 12, embodiments can, but need not necessarily include, a microprocessor (53) including a processor (54) communicatively coupled to a non-transitory memory (55) containing a program code (56) executable to produce sound (57) (depicted by arrow A7) through a speaker (58). The microprocessor (53) can be located on an appropriate location of the airway assist device (1). The program code (54) when executed can produce sound (57), which can be a prerecorded message which assists in operation of the airway assist device (1). Embodiments can further include a user interface (59) which by user interaction (depicted by arrow A8)(as shown in the example of FIG. 12) activates the microprocessor (53). As one example, the user interface (59) can comprise and activation element (60) which can be operated to cause the microprocessor to produce sound in the form of instruction on proper use of the airway assist device (1), which instructions can be paused or replayed.

Now with primary reference to FIGS. 1 and 11 through 12, a method of using embodiments of the airway assist device (1) can comprise, consist essentially of or consist of one or more of: slidably engaging the plunger (14) in the barrel (2) (depicted by arrows A2 and A6). The plunger (14) can be pushed inwardly in the barrel (2) toward the barrel distal end until the plunger distal end (16) has a location proximate or engages or abuts the barrel internal surface (8) at the barrel distal end (4) of the barrel (2)(depicted by arrow A6). With the face mask (30) or the receptacle (47), or the combination thereof, connected to the barrel (2) in one of the embodiments as above described, the method can further comprise inserting the throat tube (39) into the throat (T) of the subject (S)(as shown in the example of FIG. 1). The curved and flexible nature of the throat tube (39) can allow embodiments of the throat tube (39) to be inserted more readily in the curvature of the mouth (M) and throat (T) of the subject (S). The method can further comprise engaging the face mask (30) about the mouth (M) and nose (N) of the subject (S)(as shown in the example of FIG. 1). The throat tube (39) can be dimensioned such that once the face mask (30) engages the face (F) of the subject (S), the throat tube second end (41) has the proper location in the throat (T). Accordingly, the configuration of the mask (30) in relation to the configuration of the throat tube (T) acts as a stop and prevents over insertion of the throat tube (39) into the throat (T) which can cause the fluid or other material (O) to be pushed deeper into the subject's airway (A).

Upon proper positioning of the throat tube (39) within the person's throat (T), the method can further comprise outwardly drawing the plunger (14) slidably disposed within said barrel (2)(depicted by arrow A2) to generate a suction in the throat tube (39) which causes air to be drawn into the throat tube second end (41)(depicted by arrow A9)(as shown in the example of FIG. 1). The air drawn into the throat tube second end (41) assists in dislodging, expelling or drawing the fluid or other material (O) up and out of the throat (T)(depicted by arrow A10). A retainer ring (10) can prevent the plunger (14) from being removed from within the barrel (2). The transparent material of the dome (32) of the face mask (30) can allow the subject (S) or fluids and materials (O) to be observed through the dome (32). As one example, if the subject (S) has vomited or if fluid or material (O) has been transferred to the barrel interior chamber (9) of the barrel (2), the method can then further comprise removing the throat tube (39) from the throat (T) of the subject (S). The method can then further comprise inwardly pushing the plunger (14) in said barrel (2) to generate a positive pressure in the barrel (2) (depicted by arrow A6) and expelling the fluid or material (O) from said barrel (2) through the second opening (6) in the barrel distal end (4) or through the second one-way valve (29) (depicted by arrow A11). In those embodiments which include a receptacle (47), the method can further comprise collecting the fluid or material (O) expelled from said barrel (2) into the receptacle (47) fluidically coupled to said second opening (6)(depicted by arrow A12), and displacing air in the receptacle through a receptacle outlet port (48)(depicted by arrow A5). The method can further comprise filtering the displaced air through a filter (50) coupled the receptacle outlet port (depicted by arrow A13). The method can be repeated with or without removal of throat tube from the throat (T).

As can be easily understood from the foregoing, the basic concepts of the present invention may be embodied in a variety of ways. The invention involves numerous and varied embodiments of an airway assist device (1) and methods for making and using such airway assist device including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "filter" should be understood to encompass disclosure of the act of "filtering"—whether explicitly discussed or not—and, conversely, were there effectively disclosure of the act of "filtering", such a disclosure should be understood to encompass disclosure of a "filter" and even a "means for filtering." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the airway assist devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. An apparatus, comprising:
   a barrel having an open barrel proximal end and a barrel distal end having a first opening and a second opening;
   a plunger having a plunger proximal end and a plunger distal end, said plunger slidably disposed within said barrel;
   a first one-way valve included in said first opening at said barrel distal end through which fluid passes into said barrel upon outward draw of said plunger in said barrel;
   a second one-way valve coupled to said second opening through which fluid passes out of said barrel upon inward push of said plunger in said barrel;
   a face mask coupled to said first opening; and
   a receptacle coupled to said second opening, wherein said receptacle comprises a rigid receptacle or a flexible receptacle disposed between a pair of rigid receptacle end caps disposed a fixed distance apart by a cross member.

2. The apparatus of claim 1, wherein said face mask has a dome extending to a dome outer periphery configured to engage a subject, wherein said dome comprises a clear material allowing a user to observe said subject engaged to said face mask or a material drawn up from a throat of said subject.

3. The apparatus of claim 2, further comprising an annular cuff engaged to said dome outer periphery.

4. The apparatus of claim 3, wherein said annular cuff comprises an inflatable tubular member.

5. The apparatus of claim 1, wherein said face mask comprises a plurality of face masks which interchangeably couple to said first opening.

6. The apparatus of claim 5, wherein said plurality of face masks include a range of different sizes.

7. The apparatus of claim 1, further comprising
   a throat tube passing through said face mask, said throat tube having a tube first end fluidically connected to said first opening on said barrel distal end and a tube second end.

8. The apparatus of claim 7, further comprising one or more notches on a terminal edge of said throat tube second end.

9. The apparatus of claim 1, further comprising a handle coupled to said plunger proximal end.

10. An apparatus, comprising:
    a barrel having an open barrel proximal end and a barrel distal end having a first opening and a second opening;
    a plunger having a plunger proximal end and a plunger distal end, said plunger slidably disposed within said barrel;
    a first one-way valve coupled to said first opening at said barrel distal end through which fluid passes into said barrel upon outward draw of said plunger in said barrel;
    a second one-way valve coupled to said second opening through which fluid passes out of said barrel upon inward push of said plunger in said barrel;
    a face mask coupled to said first opening;
    a receptacle coupled to said second opening;
    a fluid outlet port defining an aperture disposed in said receptacle; and
    a filter coupled to said aperture disposed in said receptacle.

11. The apparatus of claim 10, wherein said filter allows passage of air and precludes passage of liquids or solids.

12. The apparatus of claim 11, further comprising a perforated filter retainer coupled to said aperture in said receptacle, said filter disposed in said perforated filter retainer.

13. The apparatus of claim 12, further comprising a perforated filter retainer closure removably or fixedly coupled to said perforated filter retainer.

14. An apparatus, comprising:
    a barrel having an open barrel proximal end and a barrel distal end having a first opening;
    a plunger having a plunger proximal end and a plunger distal end, said plunger slidably disposed within said barrel;
    a face mask coupled to said first opening;
    a plunger retainer ring having a radially inwardly directed annular lip defining a plunger retainer ring opening, said plunger retainer ring removably coupled to said barrel proximal end with said plunger extending through said plunger retainer ring opening;
    a first concentric ring and a second concentric ring encircling said plunger in spaced apart relation proximate said plunger distal end, said first or second concentric ring engageable with said annular lip of said plunger retainer ring to prevent withdrawal of said plunger from said barrel; and
    a first seal encircling said plunger proximate said plunger distal end, said first seal disposed between said first and second concentric rings.

15. The apparatus of claim 14, further comprising
    a third concentric ring encircling said plunger in adjacent spaced apart relation to said first and second concentric rings; and a second seal encircling said plunger disposed between said second concentric ring and said third concentric ring.

\* \* \* \* \*